United States Patent [19]

Bourquin et al.

[11] 4,128,549
[45] Dec. 5, 1978

[54] PRECURSORS OF 4-(1-ALKYL-4-PIPERIDYLIDENE-4H-BENZO[4,5]CYCLOHEPTA-[1,2-B]THIOPHEN-10(9H)-ONES

[75] Inventors: Jean-Pierre Bourquin, Magden; Gustav Schwarb, Allschwil; Erwin Waldvogel, Aesch, all of Switzerland

[73] Assignee: Sandoz Ltd., Basel, Switzerland

[21] Appl. No.: 765,231

[22] Filed: Feb. 3, 1977

Related U.S. Application Data

[60] Division of Ser. No. 662,124, Feb. 27, 1976, abandoned, which is a division of Ser. No. 492,008, Jul. 26, 1974, Pat. No. 3,960,894, which is a continuation of Ser. No. 324,999, Jan. 19, 1973, abandoned.

[51] Int. Cl.$^2$ .................. C07D 409/02; C07D 333/80
[52] U.S. Cl. ............................. 546/202; 260/332.3 P
[58] Field of Search ..................... 260/293.57, 332.3 P

[56] References Cited

U.S. PATENT DOCUMENTS

| | | | |
|---|---|---|---|
| 3,491,103 | 1/1970 | Jucker et al. | 260/293.57 |
| 3,682,930 | 8/1972 | Bourquin et al. | 260/293.57 |

FOREIGN PATENT DOCUMENTS 1169755  11/1969  United Kingdom ............. 260/332.3 P

OTHER PUBLICATIONS

Morrison, R., et al., *Organic Chemistry*, Allyn and Bacon, Inc., Boston, 1959, p. 111.

*Primary Examiner*—John D. Randolph
*Assistant Examiner*—Richard A. Schwartz
*Attorney, Agent, or Firm*—Gerald D. Sharkin; Robert S. Honor; Timothy G. Rothwell

[57] ABSTRACT

The present invention concerns a novel process for the production of known benzocycloheptathiophene derivatives of the formula:

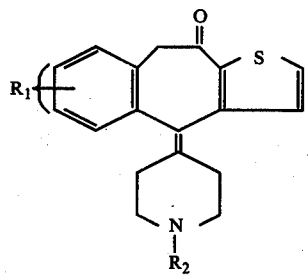

wherein $R_1$ is hydrogen, chlorine, bromine or alkoxy, and $R_2$ is alkyl. The compounds are useful as specific histaminolytics for use in the treatment of allergic conditions.

11 Claims, No Drawings

PRECURSORS OF 4-(1-ALKYL-4-PIPERIDYLIDENE-4H-BENZO[4,5-]CYCLOHEPTA-[1,2-B]THIOPHEN-10(9H)-ONES

This is a division of application Ser. No. 662,124, filed Feb. 27, 1976, now abandoned; which in turn is a division of application Ser. No. 492,008, filed July 26, 1974, now U.S. Pat. No. 3,960,894, which in turn is a continuation of application Ser. No. 324,999, filed Jan. 19, 1973, now abandoned.

The present invention relates to a process for the production of heterocyclic compounds, and more specifically to a process for the production of benzocycloheptathiophene derivatives.

The present invention provides a process for the production of a compound of formula I,

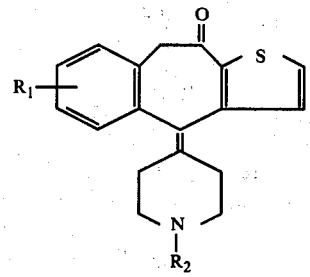

wherein
$R_1$ is in the 6 or 7 position of the benzocycloheptathiophene nucleus and is hydrogen, chlorine, bromine or alkoxy of 1 to 4 carbon atoms, and
$R_2$ is alkyl of 1 to 4 carbon atoms, which comprises dehydrating a compound of formula XI,

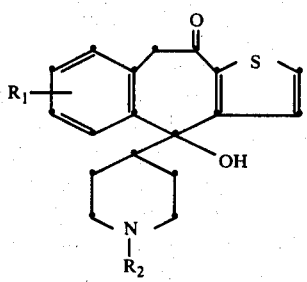

wherein
$R_1$ and $R_2$ are as defined above, $R_1$ being in the 6 or 7 position of the benzocycloheptathiophene nucleus.

The compounds of formula I may exist in either free base or acid addition salt form. Acid addition salt forms may be produced from free base forms in manner known per se and vice versa.

The dehydration of a compound of formula XI to a compound of formula I may be effected by treatment with a suitable dehydrating agent, preferably a strong acid, e.g. a strong mineral acid such as sulphuric acid, hydrochloric acid or phosphoric acid, or a strong organic acid such as trifluoroacetic acid, trichloroacetic acid or an aliphatic or aromatic sulphonic acid. The dehydration may be effected at elevated temperature, e.g. at the reflux temperature of the reaction mixture or at about 100° C employing a steam bath. The duration of the reaction will vary depending on the reaction conditions. However, a reaction period of up to 3 hours, e.g. ½ hour, is generally sufficient. Working up is effected in known manner.

The invention further provides a process for the production of a compound of formula XI, which comprises hydrolysis of the enol ether group of the compound of formula VII,

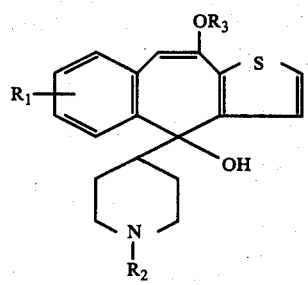

wherein
$R_1$ and $R_2$ are as defined above, $R_1$ being in the 6 or 7 position of the benzocycloheptathiophene nucleus, and
$R_3$ is alkyl of 1 to 4 carbon atoms.

The hydrolysis of the enol ether group of the compound of formula VII to obtain a compound of formula XI may be effected by treating a compound of formula VII with a hydrolysing agent such as a weak acid, e.g. acetic acid. The reaction may be effected at an elevated temperature, e.g. 100° C. The reaction duration is dependent on the reaction conditions. In general, however, a period of about ½ hour is sufficient.

Alternatively and preferably, the hydrolysis of the enol ether group of the compound of formula VII, and the subsequent dehydration of the tertiary alcohol group of formula XI to obtain a compound of formula I, is effected as a single step without isolation of any intermediate compound by treatment of the compound of formula VII with a strong aqueous acid, e.g. a strong mineral acid such as sulphuric acid, hydrochloric acid, hydrobromic acid or phosphoric acid, or a strong organic acid such as trifluoroacetic acid, trichloroacetic acid or an aliphatic or aromatic sulphonic acid, under the reaction conditions described above for the production of a compound of formula I from a compound of formula XI.

The invention also provides a process for the production of a compound of formula VII, which comprises reacting a compound of formula V,

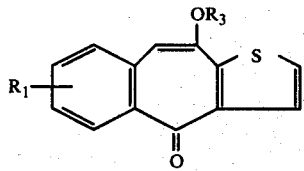

wherein
$R_1$ and $R_3$ are as defined above, $R_1$ being in the 6 or 7 position of the benzocycloheptathiophene nucleus, with a compound of formula VI,

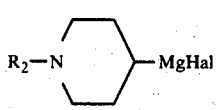

wherein

R$_2$ is as defined above, and Hal is chlorine, bromine or iodine, under Grignard conditions.

The introduction of a tert. alcohol function into the keto-enol ether of formula V is a Grignard reaction and is effected in conventional manner.

This stage of the process may, for example, be effected by adding dropwise a solution of a compound of formula V in a suitable organic solvent to a solution of a compound of formula VI in a suitable organic solvent, and allowing the reaction mixture to stand at room temperature for some time. The reaction mixture may then be heated, e.g. to the boil, and the reaction product isolated from the solution. Working up and purification may be effected in manner known per se.

The invention still further provides a process for the production of a compound of formula V, which comprises splitting off the acid HX, wherein X is chlorine or bromine, from a compound of formula IV,

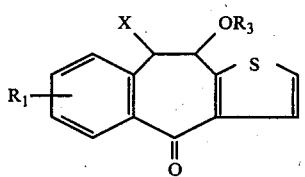

wherein

R$_1$, R$_3$ and X are as defined above, R$_1$ being in the 6 or 7 position of the benzocyclohepthiophene nucleus.

The splitting off of the acid HX from a compound of formula IV to obtain a compound of formula V may be effected under alkaline conditions, e.g. by treating a compound of formula IV with a solution of potassium hydroxide in an inert solvent, e.g. methanol. The reaction may be effected at elevated temperature, e.g. under reflux. The reaction duration will vary depending on the reaction conditions, but generally a reaction period of e.g. about 6 hours is sufficient. Working up may be effected in manner known per se.

Also provided by the present invention is a process for the production of a compound of formula IV, which comprises reacting a compound of formula II,

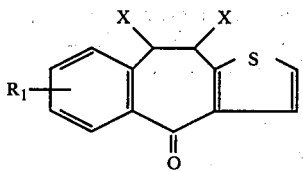

wherein

R$_1$ and X are as defined above, R$_1$ being in the 6 or 7 position of the benzocycloheptathiophene nucleus, with a compound of formula III,

R$_3$OH      III wherein R$_3$ is as defined above.

The reaction of a compound of formula II with a compound of formula III may be effected by heating together the two compounds. The compound of formula III is preferably employed as solvent. The compounds may be heated under reflux. The reaction duration will vary with the reaction conditions. However, in general, a reaction period of e.g. about 5 hours is sufficient. The addition of about 1 mol of AgNO$_3$ is found to catalyse the reaction. When AgNO$_3$ is employed, heating is not required and the reaction proceeds at room temperature. Working up may be effected in manner known per se.

It is to be noted that the introduction of the ether group in accordance with the process described immediately above is surprisingly specific to the 10 position of the benzocycloheptathiophene nucleus and the reaction is generally found to be practically quantitative.

The compounds of formula I have been described in the literature. They are useful because they possess pharmacological activity in animals. In particular, the compounds are useful as specific histaminolytics for use in the treatment of allergic conditions as indicated for example by a histaminolytic effect in the histamine toxicity test in guinea pigs on subcutaneous administration of from 0.004 to 0.15 mg/kg animal body weight, with no significant antiserotonin or anticholinergic activity at the same dosages as histaminolytic activity is observed, in, for example, the serotonin toxicity test and in the acetylcholine toxicity test in guinea pigs on subcutaneous administration of from 0.004 to 0.15 mg/kg animal body weight.

For the above-mentioned use, the dosage to be administered will, of course, vary depending upon the compound employed, mode of administration and treatment desired. However, in general, satisfactory results are obtained when administered at a daily dosage in the range of from 0.004 mg/kg to 0.15 mg/kg animal body weight, preferably given in divided doses 2 or 3 times daily, or in sustained release form. For the larger mammals, the total daily dosage is in the range of from about 0.25 to 10 mg of the compound, and dosage forms suitable for oral administration comprise from about 0.1 to 5 mg of the compound admixed with a solid or liquid pharmaceutical carrier or diluent.

Particularly interesting members of the compounds of formula I are 4-(1-methyl-4-piperidylidene)-4H-benzo[4,5]cyclohepta[1,2-b]thiophen-10(9H)-one, 6-chloro- and 7-chloro-4-(1-methyl-4-piperidylidene)-4H-benzo[4,5]cyclohepta[1,2-b]thiophen-10(9H)-one.

The pharmaceutically acceptable acid addition salt forms of the compounds possess the same order of activity as the free base forms. Examples of such salt forms are mineral acid addition salt forms such as the hydrochloride, hydrobromide and sulphate and organic acid addition salt forms such as the fumarate, maleate and tartrate.

The compounds may be employed in pharmaceutical composition form in association with a conventional pharmaceutical carrier or diluent.

The processes, in accordance with the invention, open up a new and advantageous route to the final compounds of formula I. Such route possesses distinct advantages over alternative, hitherto known routes.

For example, in accordance with a former route for the production of compounds of formula I, a compound of formula VI is reacted with a compound of formula VIII,

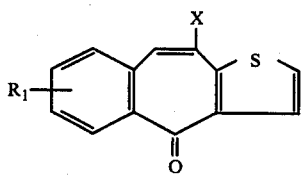

wherein

R$_1$ and X are as defined above, the resulting reaction product is converted into a compound of formula IX,

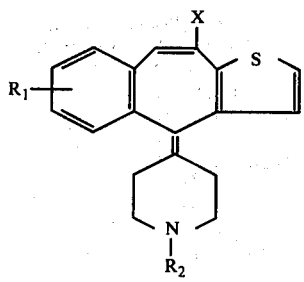

wherein

R$_1$, R$_2$ and X are as defined above, the latter compound is treated with a potassium alcoholate, and the resulting enol ether is split.

The critical stage of this process is the reaction of a compound of formula IX with an alcoholate, which proceeds as intermediate reaction via a threefold bond, whereby 9-enol ethers are mainly obtained, aside from a smaller proportion of desired 10-enol ethers. Such side reaction cannot be ascertained when compounds of formulae IV and V are used for the production of compounds of formula I.

In addition, the reaction of a compound of formula V with a compound of formula VI in the new route proceeds smoothly and gives less occasion for side reactions than the corresponding reaction of compounds of formula VI with compounds of formula VIII.

The compounds of formula IV, V, VII and XI are new and are included within the scope of the present invention.

In the following non-limitative Examples all temperatures are indicated in degrees Centigrade.

EXAMPLE 1

4-(1-Methyl-4-piperidylidene)-4H-benzo[4,5]cyclohepta[1,2-b]thiophen-10(9H)-one 3.07 g of iodine-activated magnesium shavings are covered with a layer of 25 cc of tetrahydrofuran, approximately 1/10 of a solution of 17.7 g of 4-chloro-1-methylpiperidine base in 70 cc of absolute tetrahydrofuran is added. The Grignard reaction is initiated by the addition of a few drops of 1,2-dibromoethane. The remaining 4-chloro-1-methylpiperidine solution is then added dropwise to the magnesium at such a rate that the reaction mixture boils continuously at reflux without external heating. Boiling at reflux is then continued for 1 hour. 15.3 g of 10-methoxy-4H-benzo[4,5]cyclohepta[1,2-b]thiophen-4-one (production see Examples 2 and 3) are subsequently added portion-wise at 20°, within 40 minutes, with slight cooling. After stirring at 20°for 1½ hours, the reaction solution is poured on a mixture of 180 g of ice and 20 g of ammonium chloride. The free base is extracted with chloroform. The chloroform solution is concentrated and the residue recrystallized from 270 cc of absolute ethanol. The pure 10-methoxy-4-(1-methyl-4-piperidyl)-4H-benzo[4,5]cyclohepta[1,2-b]thiophen-4-ol base, having a M.P. of 194°-196°, is obtained in this manner. Microanalysis agrees with the formula $C_{20}H_{23}NO_2S$.

A mixture of 3.4 g of 10-methoxy-4-(1-methyl-4-piperidyl)-4H-benzo[4,5]cyclohepta [1,2-b]thiophen-4-ol base and 40 cc of 3 N hydrochloric acid is kept in a boiling water bath at 95°-100° for 1 hour. The mixture is subsequently made alkaline with concentrated caustic soda solution at 20° while cooling, and the free base is extracted with chloroform. The chloroform solution is concentrated, with the residue is recrystallized from ethanol/water 1:1. The pure 4-(1-methyl-4-piperidylidene)-4H-benzo[4,5]cyclohepta[1,2-b]thiophen-10(9H)-one base, having a M.P. of 152°-153°, is obtained in this manner. Microanalysis agrees with the formula $C_{19}H_{19}NOS$. The structure was ascertained with the infrared, nuclear magnetic resonance and mass spectrograph spectra.

By employing aqueous acetic acid instead of 3 N hydrochloric acid, and heating the reaction mixture for ½ hour, the intermediate 4-(1-methyl-4-piperidyl)-4H-benzo[4,5]cyclohepta[1,2-b]thiophen-4-ol-10-one may be isolated and converted, as a separate step, to the final compound by reaction with 3 N hydrochloric acid at 100° C for ½ hour.

Proceeding in a manner analogous to that described in Example 1, and using 6-chloro-10-methoxy-4H-benzo[4,5]cyclohepta [1,2-b]thiophen-4-one, 6-chloro-4-(1-methyl-4-piperidylidene)-4H-benzo[4,5]cyclohepta[1,2-b]thiophen-10(9H)-one (M.P. 168°-169°) is obtained, (6-chloro-10-methoxy-4-(1-methyl-4-piperidyl)-4H-benzo-[4,5]cyclohepta[1,2-b]thiophen-4-ol which is obtained as an intermediate has a M.P. of 200°-202°); using 7-chloro-10-methoxy-4H-benzo[4,5]cyclohepta [1,2-b]thiophen-4-one, 7-chloro-4-(1-methyl-4-piperidylidene)-4H-benzo[4,5]cyclohepta[1,2-b]thiophen-10(9H)-one (M.P. 150°-151°) is obtained, (7-chloro-10-methoxy-4-(1-methyl-4-piperidyl)-4H-benzo[4,5]cyclohepta[1,2-b]thiophen-4-ol which is obtained as an intermediate has a M.P. of 223°-227°);

using 6-bromo-10-methoxy-4H-benzo[4,5]cyclohepta [1,2-b]thiophen-4-one, 6-bromo-4-(1methyl-4-piperidylidene)-4H-benzo[4,5]cyclohepta[1,2-b]thiophen-10(9H)-one (M.P. 172°-173°) is obtained;

using 7,10-dimethoxy-4H-benzo[4,5]cyclohepta[1,2-b]thiophen-4-one, 7-methoxy-4-(1-methyl-4-piperidylidene)-4H-benzo[4,5]cyclohepta[1,2-b]thiophen-10(9H)-one (M.P. 157°-158°) is obtained;

using 10-butoxy-4H-benzo[4,5]cyclohepta[1,2-b]thiophen-4-one, 4-(1-methyl-4-piperidylidene)-4H-benzo[4,5]cyclohepta[1,2-b]thiophen-10(9H)-one (M.P. 152°-153°) is obtained.

EXAMPLE 2

9-Bromo-9,10-dihydro-10-methoxy-4-H-benzo[4,5]cyclohepta[1,2-b]thiophen-4-one (compound of formula IV)

A suspension of 20 g of 9,10-dibromo-9,10-dihydro-4H-benzo[4,5]cyclohepta[1,2-b]thiophen-4-one in 400 cc of methanol is boiled at reflux for 5 hours. 9-Bromo- 9,10-dihydro-10-methoxy-4H-benzo [4,5]cyclohepta[1,2-b]-thiophen-4-one (M.P. 103°–106°) is obtained.

Proceeding in a manner analogous to that described in Example 2, and using the corresponding starting materials, the following compounds of formula IV are obtained:

9-bromo-6-chloro-9,10-dihydro-10-methoxy-4H-benzo [4,5]cyclohepta[1,2-b]thiophen-4-one (M.P. 134°–136°);

9-bromo-7-chloro-9,10-dihydro-10-methoxy-4H-benzo [4,5]cyclohepta[1,2-b]thiophen-4-one (M.P. 135°–137°);

6,9-dibromo-9,10-dihydro-10-methoxy-4H-benzo[4,5-]cyclohepta[1,2-b]thiophen-4-one;

9-bromo-9,10-dihydro-7,10-dimethoxy-4H-benzo[4,5-]cyclohepta[1,2-b]thiophen-4-one;

9-chloro-9,10-dihydro-10-methoxy-4H-benzo[4,5]cyclohepta[1,2-b]thiophen-4-one;

9-bromo-10-butoxy-9,10-dihydro-4H-benzo[4,5]cyclohepta[1,2-b]thiophen-4-one (M.P. 90°–91°) and 9-bromo-10-ethoxy-9,10-dihydro-4H-benzo[4,5]cyclohepta[1,2-b]thiophen-4-one.

EXAMPLE 3

10-Methoxy-4H-benzo[4,5]cyclohepta[1,2]thiophen-4-one (compound of formula V)

9 g of potassium hydroxide are added to a solution of 17.5 g of 9-bromo-9,10-dihydro-10-methoxy-4H-benzo[4,5]cyclohepta[1,2-b]thiophen-4-one in 400 cc of methanol, and the solution is boiled at reflux for 6 hours. After cooling to 0°–5°, the precipitated crystalline material is filtered off and recrystallized from methanol. The pure 10-methoxy-4H-benzo[4,5]cyclohepta[1,2-b]thiophen-4-one, having a M.P. of 164°–166°, is obtained in this mannner. Microanalysis agrees with the formula $C_{14}H_{10}O_2S$. The structure was ascertained with the nuclear magnetic resonance and mass spectrograph spectra.

Proceeding in a manner analogous to that described in Example 3, and using the compounds of formula IV mentioned in and under Example 2, the following compounds of formula V are obtained:

6-chloro-10-methoxy-4H-benzo[4,5]cyclohepta[1,2-b]thiophen-4-one (M.P. 220°–222°);

7-chloro-10-methoxy-4H-benzo[4,5]cyclohepta[1,2-b]thiophen-4-one (M.P. 216°–218°);

6-bromo-10-methoxy-4H-benzo[4,5]cyclohepta[1,2-b]thiophen-4-one;

7,10-dimethoxy-4H-benzo[4,5]cyclohepta[1,2-b]thiophen-4-one;

10-butoxy-4H-benzo[4,5]cyclohepta[1,2-b]thiophen-4-one (M.P. 83°–85°) and 10-ethoxy-4H-benzo[4,5]cyclohepta1,2-b]thiophen)4-one (M.P. 127°–129°).

What is claimed is:

1. A compound of the formula:

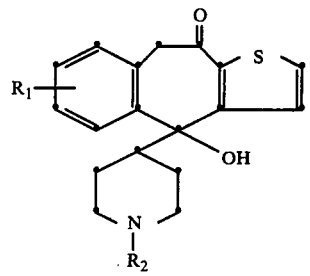

wherein
$R_1$ is in the 6 or 7 position of the benzocycloheptathiophene nucleus and is hydrogen, chlorine, bromine or alkoxy of 1 to 4 carbon atoms, and
$R_2$ is alkyl of 1 to 4 carbon atoms.

2. A compound of the formula:

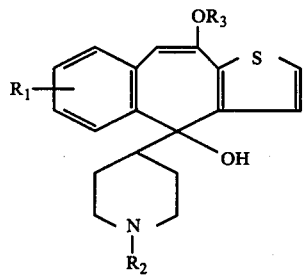

wherein
$R_1$ is in the 6 or 7 position of the cycloheptathiophene nucleus and is hydrogen, chlorine, bromine or alkoxy of 1 to 4 carbon atoms,
$R_2$ is alkyl of 1 to 4 carbon atoms, and
$R_3$ is alkyl of 1 to 4 carbon atoms.

3. The compound of claim 2, which is 10-methoxy-4-(1-methyl-4-piperidyl)-4H-benzo[4,5-]cyclohepta[1,2-b]thiophen-4-ol.

4. A compound of the formula:

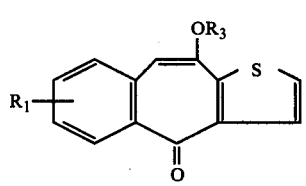

wherein
$R_1$ is in the 6 or 7 position of the cycloheptathiophene nucleus and is hydrogen, chlorine, bromine or alkoxy of 1 to 4 carbon atoms, and
$R_3$ is alkyl of 1 to 4 carbon atoms.

5. The compound of claim 4, which is 10-methoxy-4H-benzo[4,5]cyclohepta[1,2-b]thiophen-4-one.

6. The compound of claim 4 which is 6-chloro-10-methoxy-4H-benzo[4,5]cyclohepta[1,2-b]thiophen-4-one.

7. The compound of claim 4 which is 7-chloro-10-methoxy-4H-benzo[4,5]cyclohepta[1,2-b]thiophen-4-one.

8. The compound of claim 4 which is 6-bromo-10-methoxy-4H-benzo[4,5]cyclohepta[1,2-b]thiophen-4-one.

9. The compound of claim 4 which is 7,10-dimethoxy-4H-benzo[4,5]cyclohepta[1,2-b]thiophen-4-one.

10. The compound of claim 4 which is 10-butoxy-4H-benzo[4,5]cyclohepta[1,2-b]thiophen-4-one.

11. The compound of claim 4 which is 10-ethoxy-4H-benzo[4,5]cyclohepta[1,2-b]thiophen-4-one.

* * * * *